US006727376B2

(12) United States Patent
Ueno et al.

(10) Patent No.: US 6,727,376 B2
(45) Date of Patent: Apr. 27, 2004

(54) PREPARATION OF ORGANOHALOSILANES

(75) Inventors: Susumu Ueno, Takefu (JP); Toshio Shinohara, Annaka (JP); Mikio Aramata, Annaka (JP); Yoichi Tanifuji, Tokyo (JP); Tetsuya Inukai, Annaka (JP); Hajime Ishizaka, Annaka (JP)

(73) Assignee: Shin-Etsu Chemical Co., Ltd., Tokyo (JP)

( * ) Notice: Subject to any disclaimer, the term of this patent is extended or adjusted under 35 U.S.C. 154(b) by 48 days.

(21) Appl. No.: 10/230,093

(22) Filed: Aug. 29, 2002

(65) Prior Publication Data
US 2003/0055277 A1 Mar. 20, 2003

(30) Foreign Application Priority Data

Aug. 30, 2001 (JP) ........................................ 2001-261759

(51) Int. Cl.$^7$ ................................................. C07F 7/16
(52) U.S. Cl. ...................................................... 556/472
(58) Field of Search .......................................... 556/472

(56) References Cited

U.S. PATENT DOCUMENTS

| 2,380,995 A | 8/1945 | Rochow | 260/607 |
| 4,500,724 A | 2/1985 | Ward, III et al. | 556/472 |
| 4,602,101 A | 7/1986 | Halm et al. | 556/472 |
| 5,059,706 A * | 10/1991 | Degen et al. | 556/472 |
| 6,005,130 A | 12/1999 | Lewis et al. | 556/472 |
| 6,025,513 A | 2/2000 | Nakanishi et al. | 556/472 |
| 6,215,012 B1 | 4/2001 | Ueno et al. | 556/472 |
| 6,242,629 B1 | 6/2001 | Ueno et al. | 556/472 |
| 6,528,674 B1 * | 3/2003 | Lewis et al. | 556/472 |

FOREIGN PATENT DOCUMENTS

| JP | 5-51596 B2 | 8/1993 |
| JP | 6-92421 B2 | 11/1994 |
| SU | 122749 | 1/1959 |
| SU | 178817 | 3/1966 |
| SU | 237892 | 11/1969 |

OTHER PUBLICATIONS

F. Komitsky et al., Silicon for the Chemical Industry IV., Geiranger, Norway (1998), pp. 217–225.

L. Rosch, W. Kalchauer et al., Silicon for the Chemical Industry III, Sandefjord, Norway (1996), pp. 269–273.

* cited by examiner

Primary Examiner—Peter O'Sullivan
(74) Attorney, Agent, or Firm—Birch, Stewart, Kolasch & Birch, LLP

(57) ABSTRACT

In an industrial process for preparing organohalosilanes by reacting metallic silicon particles with an organohalide in the presence of a copper catalyst, a contact mass composed of the metallic silicon and the catalyst further contains an effective amount of a phosphonium compound having on the molecule at least one group of the formula: $[R^2R^3R^4P—]^+ Y^-$ wherein $R^2$, $R^3$ and $R^4$ each are a monovalent hydrocarbon group and Y is a halogen atom or acid group. The invention drastically increases the silane formation rate and the utilization of silicon without lowering the selectivity of useful silane.

4 Claims, No Drawings

PREPARATION OF ORGANOHALOSILANES

BACKGROUND OF THE INVENTION

With respect to the synthesis of alkylhalosilanes, Rochow first disclosed in U.S. Pat. No. 2,380,995 direct synthesis reaction between metallic silicon and alkyl halide in the presence of a copper catalyst. Since then, there have been reported a number of research works relating to various co-catalysts used together with copper catalysts, reactors, additives used during reaction, and the like. In the industrial synthesis of organohalosilanes, the selectivity of diorganodihalosilane which is most widely used in silicone resins, the formation rate of silanes, and the percent conversion of metallic silicon into useful silane are crucial. The selectivity of diorganodihalosilane is evaluated in terms of a weight or molar ratio of dialkyldihalosilane to the silanes produced and a T/D ratio.

Organohalosilane products contain diorganodihalosilane (D), triorganohalosilane (M), organotrihalosilane (T), etc. as well as other by-products such as organohydrodihalosilane (H) and organohalodisilane. In particular, disilanes are known as a high-boiling fraction among silicone manufacturers using direct method organohalosilanes because few processes are available for the effective utilization of disilanes, and most disilanes are discarded. The T/D ratio is a compositional ratio of organotrihalosilane to diorganodihalosilane in the entire organohalosilanes produced, with a lower T/D ratio being preferred. The formation rate of organohalosilane is represented by a space time yield (STY) which is the weight of crude organohalosilane produced per unit time relative to the weight of metallic silicon held in the reactor. In order to improve the content of diorganohalosilane produced, reduce the T/D ratio or increase the STY, various research works have been made with a focus on the catalyst and co-catalyst.

USSR Application Specification No. 617,569 (Certificate of inventorship No. 122,749) dated Jan. 24, 1959 discloses reaction in the presence of metallic silicon-copper alloy with 20 to 40 ppm of antimony added. Allegedly, the dimethyldichlorosilane content is improved from 40% to 60%. U.S. Pat. No. 4,500,724 discloses use of a copper/zinc/tin catalyst containing 200 to 3,000 ppm of tin, thereby achieving an improvement of T/D to 0.037. Japanese Patent Publication (JP-B) No. 6-92421 discloses reaction using copper arsenide having an arsenic concentration of at least 50 ppm. It is described in these patent references that reactivity, more specifically the rate of reaction of metallic silicon is improved by adding these tin, antimony and arsenic co-catalysts to a reaction contact mass comprising metallic silicon and copper.

USSR Application Specification No. 903,369 (Certificate of inventorship No. 178,817) dated Jun. 2, 1964 discloses that a co-catalyst selected from the group consisting of zinc, bismuth, phosphorus (200 ppm), arsenic, tin, and iron improves the dimethyldichlorosilane content to 72.1% from the value of 40–60% achieved by the above-referred Application Specification No. 617,569 (Certificate of inventorship No. 122,749). Also USSR Application Specification No. 1,152,943 (Certificate of inventorship No. 237,892) dated Nov. 20, 1969 discloses to add a phosphorus-copper-silicon alloy to a contact mass so as to give 2,500 to 30,000 ppm of phosphorus, thereby improving the dimethyldichlorosilane content to 82.3%. Moreover, U.S. Pat. No. 4,602,101 corresponding to JP-B 5-51596 discloses that 25 to 2,500 ppm of a phosphorus compound capable of generating elemental phosphorus in the reactor is added to a contact mass. Although the results of reaction according to this US patent are improved over the last-mentioned USSR patent, there still remain many problems including hazard imposed by spontaneously igniting elemental phosphorus and increased cost of raw materials. Then this US patent is also unsuitable to apply to commercial scale reactors. Also, F. Komitsky et al., Silicon For the Chemical Industry IV, Geiranger, Norway (1998), page 217, proposes the addition of phosphorus in the form of copper phosphide, leaving problems including a low percent conversion, ineffective utilization of phosphorus, and difficult control of a phosphorus concentration. U.S. Pat. No. 6,025,513 intends to add boron to a contact mass wherein the boron concentration is controlled so as to improve productivity. U.S. Pat. No. 5,059,706 discloses to introduce a phosphorus compound in a vapor phase into a reactor for increasing selectivity. U.S. Pat. No. 6,005,130 discloses to introduce organomonophosphine for increasing selectivity.

However, the phosphorus base additives used in the prior art have an outstanding trade-off between activity and composition selectivity. In particular, it is pointed out that oxide originating from phosphorus can exacerbate flow on the particle surface. Therefore, the conventional phosphorus base additives offer few merits on the continuous operation of commercial scale reactors. Other additives are known from L. Rosch, W. Kalchauer et al., Silicon for the Chemical Industry IV, Sandefjord, Norway (1996) wherein monomethyldichlorosilane is introduced for improving activity. This additive is effective only at the initial period, but not regarded as exerting a lasting effect during the continuous operation of commercial scale reactors.

Also, since the gas phase low-molecular weight compounds used in the prior art have a low evaporation temperature and lack thermal stability, it is difficult to precisely control the reaction at elevated temperatures. Under such circumstances, Ueno et al. proposed from a different point of view which had never been taken in the prior art, an industrial process using organophosphino compounds as the activating agent (see U.S. Pat. Nos. 6,215,012 and 6,242,629).

SUMMARY OF THE INVENTION

An object of the invention is to provide a novel and improved process for preparing organohalosilanes at a drastically increased formation rate without lowering the selectivity of useful silane, thereby increasing the utilization of silicon.

The present invention provides a process for preparing organohalosilanes of the following general formula (I):

$$R^1_n H_m SiX_{4-n-m} \tag{I}$$

wherein $R^1$ is a monovalent hydrocarbon group, X is a halogen atom, n is an integer of 1 to 3, m is an integer of 0 to 2, and the sum of n and m is an integer of 1 to 3, by reacting metallic silicon particles with an organohalide in the presence of a copper catalyst, wherein a contact mass composed of the metallic silicon and the catalyst further contains an effective amount of a phosphonium compound having on the molecule at least one group of the following general formula (II):

$$[R^2 R^3 R^4 P\text{—}]^+ Y^- \tag{II}$$

wherein $R^2$, $R^3$ and $R^4$ are each independently a monovalent hydrocarbon group and Y is a halogen atom or acid group.

In summary, in the synthesis of organohalosilanes by reaction of metallic silicon with organohalide, the present invention incorporates an effective amount of a specific phosphonium compound in the contact mass for the purpose of increasing the formation rate of useful silane. More particularly, conventional additives which are known effective to improve the useful silane content are phosphorus compounds including metallic phosphorus, phosphorus oxide, copper phosphide, tin phosphide, zinc phosphide, aluminum phosphide, antimony phosphide, phosphorus trichloride, trimethylphosphine, and triphenylphosphine. We addressed the actual drawback of the direct method or Rochow method using such phosphorus compounds as a co-catalyst, that is, the problem that the phosphorus compounds serve to increase the diorganodihalosilane content, but reduce the reaction rate and hence, the productivity of useful silane. We also intended to realize in a commercial plant an increase of production rate which has never been accomplished when the direct method is carried out using as an activator conventional additives known to improve activity or such compounds as methyldichlorosilane. In such efforts, we have found that the above objects are attained by adding phosphonium compounds, which are less expensive and economically more advantageous than the organophosphine compounds, to the contact mass.

The process of the invention is by adding a catalytic amount of a specific phosphonium compound to a contact mass which becomes effective, independent of the form of copper catalyst, for increasing the reaction rate of Rochow reaction, without catalyzing side reaction and without decreasing the yield of the main component, diorganodihalosilane. The production rate of useful silane is thus improved while the catalysis of the phosphonium compound lasts long. In this sense, the present invention is completely different from the prior art improvements which are formulations relying on the short-lived effects of catalysts.

The inventors assumed that a phosphonium compound, when added in a very small amount, attacks the primary catalyst, copper to create copper halide which is necessary to induce Rochow reaction active site-forming reaction, while the phosphonium compound itself converts to a phosphine compound which does not catalyze side reaction. Based on this assumption, we made a study on a series of phosphonium compound. We have discovered that in the synthesis of organohalosilanes by reaction of metallic silicon with organohalide, a contact mass containing an effective amount of the phosphonium compound is effective for increasing the production rate for thereby increasing the utilization of silicon without reducing the proportion of useful silane. That is, the present invention is predicated on the discovery that a contact mass containing a very small, but effective amount of the phosphonium compound can significantly increase the production rate without substantially changing the useful silane content.

DESCRIPTION OF THE PREFERRED EMBODIMENT

The process for preparing organohalosilanes according to the invention involves the step of reacting metallic silicon particles with an organohalide in the presence of a copper catalyst to thereby form organohalosilanes of the following general formula (I):

$$R^1_n H_m SiX_{4-n-m} \quad (I)$$

wherein $R^1$ is a monovalent hydrocarbon group, X is a halogen atom, n is an integer of 1 to 3, m is an integer of 0 to 2, and n+m is an integer of 1 to 3.

In formula (I), suitable monovalent hydrocarbon groups represented by $R^1$ include $C_{1-6}$ alkyl, alkenyl and aryl groups, preferably methyl and phenyl, with methyl being most preferred. It is preferred that n is 2, m is 0 and n+m=2. X is preferably chlorine or bromine, with chlorine being more preferred.

The metallic silicon used herein preferably has a silicon purity of at least 97% by weight, especially at least 98% by weight. Prior to use, the metallic silicon is preferably ground into particles with an appropriate particle size. Where the reactor used is a fluidized bed or stirred bed reactor, the metallic silicon powder should preferably have a particle size in the range of 5 to 150 μm, corresponding to 50% of the weight base cumulative size distribution curve on sieving, in order that the metallic silicon powder have good fluidity.

Illustrative examples of the organohalide to be reacted with metallic silicon to form organohalosilanes include methyl chloride, ethyl chloride, propyl chloride, methyl bromide, ethyl bromide, benzene chloride and benzene bromide. Of these, methyl chloride and benzene chloride are preferable in the industry. Methyl chloride is most useful because organohalosilanes, typically dimethyldichlorosilane, produced therefrom find a wide variety of applications as the raw material for many silicone resins.

The copper catalyst used herein may be selected from various forms of copper including elemental copper (or metallic copper) such as powdered copper and stamped copper, and copper compounds such as cuprous oxide, cupric oxide, and copper halides. Any of promoters such as zinc, tin, antimony and arsenic may be used as the co-catalyst. The co-catalyst may be used alone or in the form of an alloy with copper. Examples of the co-catalyst include metallic zinc, zinc compounds such as zinc-copper alloys, zinc chloride, zinc oxide, and zinc acetate, metallic tin, tin compounds such as tin-copper alloys, tin chloride and tin oxide, metallic antimony, antimony compounds such as antimony chloride and antimony oxide, metallic aluminum, aluminum compounds such as aluminum chloride and aluminum oxide, metallic phosphorus, inorganic phosphorus compounds such as phosphorus trichloride and phosphorus oxide, and organic phosphorus compounds, for example, monoalkylphosphines such as trimethylphosphine and triphenylphosphine. Suitable combinations of the copper catalyst with the co-catalyst are copper alloys including Cu—Zn, Cu—Sn, and Cu—Zn—Sn (or Sb or As) as mentioned above.

The copper catalyst may be admitted alone into the reactor. The amounts of the copper catalyst and co-catalyst used are effective amounts. An appropriate amount of the copper catalyst blended is about 0.1 to 10 parts, and more preferably about 2 to 8 parts by weight, calculated as copper, per 100 parts by weight of the metallic silicon powder. As to the co-catalyst, it is preferred that zinc is used in an amount of 0.05 to 1 part by weight; tin or antimony is used in an amount of 0.001 to 0.05 part, especially 0.005 to 0.01 part by weight; aluminum is used in an amount of 0.005 to 1 part, especially 0.01 to 0.5 part by weight; and phosphorus is used in an amount of 0.001 to 1 part, especially 0.005 to 0.7 part by weight, each per 100 parts by weight of the metallic silicon powder. In the case of compounds such as zinc compounds, they are preferably added so as to provide the respective metals in the above-described amounts. A mixture of two or more co-catalysts may be used.

According to the invention, the contact mass composed of metallic silicon particles, the copper catalyst and optionally, the co-catalyst further contains an effective amount of a phosphonium compound having per molecule at least one group of the following general formula (II):

$$[R^2R^3R^4P—]^+Y^-  \quad (II)$$

wherein each of $R^2$, $R^3$ and $R^4$ which may be the same or different is a monovalent hydrocarbon group and Y is a halogen atom or acid group.

Suitable monovalent hydrocarbon groups represented by $R^2$, $R^3$ and $R^4$ include $C_{1-10}$ alkyl, aryl and alkenyl groups, with $C_{1-4}$ alkyl and phenyl groups being preferred. Examples of the halogen atom or acid group represented by Y include chlorine, bromine and fluorine, with chlorine being preferred.

Typical phosphonium compounds have the following general formula (III):

$$[R^5R^6R^7R^8P]^+Y^- \quad (III)$$

wherein each of $R^5$, $R^6$, $R^7$ and $R^8$ which may be the same or different is a monovalent hydrocarbon group and Y is as defined above. Like $R^1$ to $R^4$, the monovalent hydrocarbon groups represented by $R^5$ to $R^8$ are often $C_{1-10}$ alkyl, aryl and alkenyl groups. Preferred among others are a phosphonium compound having the formula:

$$R^9{}_4PCl$$

wherein $R^9$ is a $C_{1-4}$ alkyl or phenyl group and a phosphonium compound having the formula:

$$[(R^{10}{}_2N)_3PN]_4PCl$$

wherein $R^{10}$ is a $C_{1-4}$ alkyl group.

Preferred examples of the phosphonium compound include tetramethylphosphonium chloride, tetramethylphosphonium bromide, tetraethylphosphonium chloride, tetraethylphosphonium bromide, tetra-n-butylphosphonium chloride, tetra-n-butylphosphonium bromide, tetra-n-butylphosphonium hydrogen difluoride, tetraphenylphosphonium chloride, tetraphenylphosphonium bromide, tetraphenylphosphonium iodide, tetraphenylphosphonium fluoride, methyltriphenylphosphonium chloride, methyltriphenylphosphonium bromide, ethyltriphenylphosphonium chloride, ethyltriphenylphosphonium bromide, n-butyltriphenylphosphonium chloride, n-butyltriphenylphosphonium bromide, benzyltriphenylphosphonium chloride, benzyltriphenylphosphonium bromide, and tetrakis[tris(dimethylamino)phosphoranylideneamino]-phosphonium chloride.

To improve the productivity of organohalosilane, an effective amount of the phosphonium compound is used, the effective amount being determined on the basis of the entire amount of silicon and depending on the reaction time, scale and grade of metallic silicon. Preferably 0.1 to 25,000 parts, and especially 1 to 5,000 parts by weight of the phosphonium compound is used per million parts by weight of metallic silicon powder.

In the contact mass, an anti-agglomerating agent such as silica, diatomaceous earth, mica, talc, alumina, titanium oxide and carbon may be included in order to prevent the contact mass from agglomerating. If desired, hydrogen, hydrogen chloride gas, hydrosilane or chlorosilane may be fed in order to control the composition or activity of the contact mass.

In carrying out the process for preparing organohalosilanes according to the invention, any well-known method may be used except for the use of the phosphonium compound. More specifically, when Rochow reaction is carried out between an organohalide and a contact mass including metallic silicon, copper or copper compound and optionally, a co-catalyst such as Zn, Sn, Sb, Al, P or compound thereof at a temperature in the range of about 250 to 600° C., the phosphonium compound is added to the contact mass whereby diorganohalosilanes of formula (I) are produced at a significantly increased production rate or space time yield (STY).

The process of the invention can be carried out in any of fixed bed reactors, stirred bed reactors and fluidized bed reactors. From the industrial aspect, a fluidized bed reactor suited for continuous operation is employed.

The organohalide is previously heated and gasified before it is fed into the reactor. The organohalide gas may be fed alone or along with an inert gas in a sufficient amount to fluidize the contact mass. The fluidizing amount is determined as appropriate from the diameter of the reactor and the superficial velocity.

In the step of heating the contact mass or imparting catalytic activity to the contact mass, an inert gas is used for fluidizing the contact mass in the reactor. Such an inert gas may be nitrogen, helium or argon gas, for example, with the nitrogen gas being preferable from the economic standpoint. The flow velocity of the inert gas fed in this and subsequent steps is at least the incipient fluidization velocity of the contact mass, and preferably about 5 times the incipient fluidization velocity. A flow velocity below the range of the inert gas may often fail to achieve uniform fluidization of the contact mass. If the flow velocity of the inert gas is above the range, metallic silicon powder may be excessively scattered with increased losses of the inert gas and heat. It is recommended to recycle the inert gas and the organohalide.

After the contact mass is given catalytic activity as mentioned above, the organohalide is introduced into the reactor where gas-solid catalytic reaction takes place between the organohalide and metallic silicon to form organohalosilanes.

EXAMPLE

Examples of the invention are given below by way of illustration and not by way of limitation. Parts are by weight.

Comparative Example 1

A fluidized bed reactor of carbon steel having a diameter of 75 mm and a height of 900 mm was charged with 100 parts of metallic silicon powder and 4 parts of a catalyst in the form of metallic copper powder. Then a gas mixture of methyl chloride and nitrogen was introduced into the reactor at a rate of 14.4 Nl/min and the reactor was heated at a temperature of 310° C. whereupon reaction continued. A mixture of metallic silicon powder and the catalyst was fed from the reactor bottom so as to keep constant the amount of the contact mass in the reactor. Reaction was continued for 6 hours, following which the reaction was terminated. The run was repeated 6 times. Reported in Table 1 are the concentrations of impurities in the metallic silicon used, an average of silane formation rate from the start to the end of reaction, and an average of cumulative content of useful silane.

Comparative Example 2

A fluidized bed reactor of carbon steel having a diameter of 75 mm and a height of 900 mm was charged with 100 parts of metallic silicon powder and 5 parts of a catalyst in the form of copper oxide powder. Then a gas mixture of methyl chloride and nitrogen was introduced into the reactor at a rate of 14.4 Nl/min and the reactor was heated at a temperature of 320° C. whereupon reaction continued. A mixture of metallic silicon powder and the catalyst was fed from the reactor bottom so as to keep constant the amount of the contact mass in the reactor. Reaction was continued for 6 hours, following which the reaction was terminated. The run was repeated 2 times. Reported in Table 1 are the concentrations of impurities in the metallic silicon used, an average of silane formation rate from the start to the end of reaction, and an average of cumulative content of useful silane.

Example 1

A fluidized bed reactor of carbon steel having a diameter of 75 mm and a height of 900 mm was charged with 100 parts of metallic silicon powder, 4 parts of a catalyst in the form of metallic copper powder, and 0.15 part of tetraethylphosphonium chloride $(C_2H_5)_4PCl$. Then a gas mixture of methyl chloride and nitrogen was introduced into the reactor at a rate of 14.4 Nl/min and the reactor was heated at a temperature of 310° C. whereupon reaction continued. A mixture of metallic silicon powder and the catalyst was fed from the reactor bottom so as to keep constant the amount of the contact mass in the reactor. Reaction was continued for 6 hours, following which the reaction was terminated. The run was repeated 2 times. Reported in Table 1 are the concentrations of impurities in the metallic silicon used, an average of silane formation rate from the start to the end of reaction, and an average of cumulative content of useful silane.

Example 2

A fluidized bed reactor of carbon steel having a diameter of 75 mm and a height of 900 mm was charged with 100 parts of metallic silicon powder, 5 parts of a catalyst in the form of copper oxide powder, and 0.15 part of tetraethylphosphonium chloride $(C_2H_5)_4PCl$. Then a gas mixture of methyl chloride and nitrogen was introduced into the reactor at a rate of 14.4 Nl/min and the reactor was heated at a temperature of 320° C. whereupon reaction continued. A mixture of metallic silicon powder and the catalyst was fed from the reactor bottom so as to keep constant the amount of the contact mass in the reactor. Reaction was continued for 6 hours, following which the reaction was terminated. The run was repeated 2 times. Reported in Table 1 are the concentrations of impurities in the metallic silicon used, an average of silane formation rate from the start to the end of reaction, and an average of cumulative content of useful silane.

Example 3

A fluidized bed reactor of carbon steel having a diameter of 75 mm and a height of 900 mm was charged with 100 parts of metallic silicon powder, 4 parts of a catalyst in the form of metallic copper powder, and 0.05 part of tetraethylphosphonium chloride $(C_2H_5)_4PCl$. Then a gas mixture of methyl chloride and nitrogen was introduced into the reactor at a rate of 14.4 Nl/min and the reactor was heated at a temperature of 310° C. whereupon reaction continued. A mixture of metallic silicon powder and the catalyst was fed from the reactor bottom so as to keep constant the amount of the contact mass in the reactor. Reaction was continued for 12 hours, following which the reaction was terminated. The run was repeated 2 times. Reported in Table 1 are the concentrations of impurities in the metallic silicon used, an average of silane formation rate from the start to the end of reaction, and an average of cumulative content of useful silane.

Example 4

A fluidized bed reactor of carbon steel having a diameter of 75 mm and a height of 900 mm was charged with 100 parts of metallic silicon powder, 5 parts of a catalyst in the form of copper oxide powder, and 0.05 part of tetraethylphosphonium chloride $(C_2H_5)_4PCl$. Then a gas mixture of methyl chloride and nitrogen was introduced into the reactor at a rate of 14.4 Nl/min and the reactor was heated at a temperature of 320° C. whereupon reaction continued. A mixture of metallic silicon powder and the catalyst was fed from the reactor bottom so as to keep constant the amount of the contact mass in the reactor. Reaction was continued for 12 hours, following which the reaction was terminated. The run was repeated 2 times. Reported in Table 1 are the concentrations of impurities in the metallic silicon used, an average of silane formation rate from the start to the end of reaction, and an average of cumulative content of useful silane.

Example 5

A fluidized bed reactor of carbon steel having a diameter of 75 mm and a height of 900 mm was charged with 100 parts of metallic silicon powder, 4 parts of a catalyst in the form of metallic copper powder, and 0.24 part of tetrabutylphosphonium chloride $(C_4H_9)_4PCl$. Then a gas mixture of methyl chloride and nitrogen was introduced into the reactor at a rate of 14.4 Nl/min and the reactor was heated at a temperature of 310° C. whereupon reaction continued. A mixture of metallic silicon powder and the catalyst was fed from the reactor bottom so as to keep constant the amount of the contact mass in the reactor. Reaction was continued for 6 hours, following which the reaction was terminated. The run was repeated 2 times. Reported in Table 1 are the concentrations of impurities in the metallic silicon used, an average of silane formation rate from the start to the end of reaction, and an average of cumulative content of useful silane.

Example 6

A fluidized bed reactor of carbon steel having a diameter of 75 mm and a height of 900 mm was charged with 100 parts of metallic silicon powder, 5 parts of a catalyst in the form of copper oxide powder, and 0.24 part of tetrabutylphosphonium chloride $(C_4H_9)_4PCl$. Then a gas mixture of methyl chloride and nitrogen was introduced into the reactor at a rate of 14.4 Nl/min and the reactor was heated at a temperature of 320° C. whereupon reaction continued. A mixture of metallic silicon powder and the catalyst was fed from the reactor bottom so as to keep constant the amount of the contact mass in the reactor. Reaction was continued for 6 hours, following which the reaction was terminated. The run was repeated 2 times. Reported in Table 1 are the concentrations of impurities in the metallic silicon used, an average of silane formation rate from the start to the end of reaction, and an average of cumulative content of useful silane.

Example 7

A fluidized bed reactor of carbon steel having a diameter of 75 mm and a height of 900 mm was charged with 100 parts of metallic silicon powder, 4 parts of a catalyst in the form of metallic copper powder, and 0.06 part of tetrabutylphosphonium chloride $(C_4H_9)_4PCl$. Then a gas mixture of methyl chloride and nitrogen was introduced into the reactor at a rate of 14.4 Nl/min and the reactor was heated at a temperature of 310° C. whereupon reaction continued. A mixture of metallic silicon powder and the catalyst was fed from the reactor bottom so as to keep constant the amount of the contact mass in the reactor. Reaction was continued for 12 hours, following which the reaction was terminated. The run was repeated 2 times. Reported in Table 1 are the concentrations of impurities in the metallic silicon used, an average of silane formation rate from the start to the end of reaction, and an average of cumulative content of useful silane.

Example 8

A fluidized bed reactor of carbon steel having a diameter of 75 mm and a height of 900 mm was charged with 100 parts of metallic silicon powder, 5 parts of a catalyst in the form of copper oxide powder, and 0.06 part of tetrabutylphosphonium chloride $(C_4H_9)_4PCl$. Then a gas mixture of methyl chloride and nitrogen was introduced into the reactor at a rate of 14.4 Nl/min and the reactor was heated at a temperature of 320° C. whereupon reaction continued. A mixture of metallic silicon powder and the catalyst was fed from the reactor bottom so as to keep constant the amount of the contact mass in the reactor. Reaction was continued for 12 hours, following which the reaction was terminated. The run was repeated 2 times. Reported in Table 1 are the concentrations of impurities in the metallic silicon used, an average of silane formation rate from the start to the end of reaction, and an average of cumulative content of useful silane.

Example 9

A fluidized bed reactor of carbon steel having a diameter of 75 mm and a height of 900 mm was charged with 100 parts of metallic silicon powder, 4 parts of a catalyst in the form of metallic copper powder, and 0.30 part of tetraphenylphosphonium chloride $(C_6H_5)_4PCl$. Then a gas mixture of methyl chloride and nitrogen was introduced into the reactor at a rate of 14.4 Nl/min and the reactor was heated at a temperature of 310° C. whereupon reaction continued. A mixture of metallic silicon powder and the catalyst was fed from the reactor bottom so as to keep constant the amount of the contact mass in the reactor. Reaction was continued for 6 hours, following which the reaction was terminated. The run was repeated 2 times. Reported in Table 1 are the concentrations of impurities in the metallic silicon used, an average of silane formation rate from the start to the end of reaction, and an average of cumulative content of useful silane.

Example 10

A fluidized bed reactor of carbon steel having a diameter of 75 mm and a height of 900 mm was charged with 100 parts of metallic silicon powder, 5 parts of a catalyst in the form of copper oxide powder, and 0.30 part of tetraphenylphosphonium chloride $(C_6H_5)_4PCl$. Then a gas mixture of methyl chloride and nitrogen was introduced into the reactor at a rate of 14.4 Nl/min and the reactor was heated at a temperature of 320° C. whereupon reaction continued. A mixture of metallic silicon powder and the catalyst was fed from the reactor bottom so as to keep constant the amount of the contact mass in the reactor. Reaction was continued for 6 hours, following which the reaction was terminated. The run was repeated 2 times. Reported in Table 1 are the concentrations of impurities in the metallic silicon used, an average of silane formation rate from the start to the end of reaction, and an average of cumulative content of useful silane.

Example 11

A fluidized bed reactor of carbon steel having a diameter of 75 mm and a height of 900 mm was charged with 100 parts of metallic silicon powder, 4 parts of a catalyst in the form of metallic copper powder, and 0.05 part of tetraphenylphosphonium chloride $(C_6H_5)_4PCl$. Then a gas mixture of methyl chloride and nitrogen was introduced into the reactor at a rate of 14.4 Nl/min and the reactor was heated at a temperature of 310° C. whereupon reaction continued. A mixture of metallic silicon powder and the catalyst was fed from the reactor bottom so as to keep constant the amount of the contact mass in the reactor. Reaction was continued for 12 hours, following which the reaction was terminated. The run was repeated 2 times. Reported in Table 1 are the concentrations of impurities in the metallic silicon used, an average of silane formation rate from the start to the end of reaction, and an average of cumulative content of useful silane.

Example 12

A fluidized bed reactor of carbon steel having a diameter of 75 mm and a height of 900 mm was charged with 100 parts of metallic silicon powder, 5 parts of a catalyst in the form of copper oxide powder, and 0.05 part of tetraphenylphosphonium chloride $(C_6H_5)_4PCl$. Then a gas mixture of methyl chloride and nitrogen was introduced into the reactor at a rate of 14.4 Nl/min and the reactor was heated at a temperature of 320° C. whereupon reaction continued. A mixture of metallic silicon powder and the catalyst was fed from the reactor bottom so as to keep constant the amount of the contact mass in the reactor. Reaction was continued for 12 hours, following which the reaction was terminated. The run was repeated 2 times. Reported in Table 1 are the concentrations of impurities in the metallic silicon used, an average of silane formation rate from the start to the end of reaction, and an average of cumulative content of useful silane.

Example 13

A fluidized bed reactor of carbon steel having a diameter of 75 mm and a height of 900 mm was charged with 100 parts of metallic silicon powder, 4 parts of a catalyst in the form of metallic copper powder, and 0.10 part of tetramethylphosphonium chloride $(CH_3)_4PCl$. Then a gas mixture of methyl chloride and nitrogen was introduced into the reactor at a rate of 14.4 Nl/min and the reactor was heated at a temperature of 330° C. whereupon reaction continued. A mixture of metallic silicon powder and the catalyst was fed from the reactor bottom so as to keep constant the amount of the contact mass in the reactor. Reaction was continued for 6 hours, following which the reaction was terminated. The run was repeated 2 times. Reported in Table 1 are the concentrations of impurities in the metallic silicon used, an average of silane formation rate from the start to the end of reaction, and an average of cumulative content of useful silane.

Example 14

A fluidized bed reactor of carbon steel having a diameter of 75 mm and a height of 900 mm was charged with 100 parts of metallic silicon powder, 5 parts of a catalyst in the form of copper oxide powder, and 0.10 part of tetramethylphosphonium chloride $(CH_3)_4PCl$. Then a gas mixture of methyl chloride and nitrogen was introduced into the reactor at a rate of 14.4 Nl/min and the reactor was heated at a temperature of 340° C. whereupon reaction continued. A mixture of metallic silicon powder and the catalyst was fed from the reactor bottom so as to keep constant the amount of the contact mass in the reactor. Reaction was continued for 6 hours, following which the reaction was terminated. The run was repeated 2 times. Reported in Table 1 are the concentrations of impurities in the metallic silicon used, an average of silane formation rate from the start to the end of reaction, and an average of cumulative content of useful silane.

Example 15

A fluidized bed reactor of carbon steel having a diameter of 75 mm and a height of 900 mm was charged with 100 parts of metallic silicon powder, 4 parts of a catalyst in the form of metallic copper powder, and 0.30 part of tetrakis [tris(dimethylamino)phosphoranylideneamino]-phosphonium chloride $[((CH_3)_2N)_3PN]_4PCl$. Then a gas mixture of methyl chloride and nitrogen was introduced into the reactor at a rate of 14.4 Nl/min and the reactor was heated at a temperature of 320° C. whereupon reaction continued. A mixture of metallic silicon powder and the catalyst was fed from the reactor bottom so as to keep constant the amount of the contact mass in the reactor. Reaction was continued for 6 hours, following which the reaction was terminated. The run was repeated 2 times. Reported in Table 1 are the concentrations of impurities in the metallic silicon used, an average of silane formation rate from the start to the end of reaction, and an average of cumulative content of useful silane.

Example 16

A fluidized bed reactor of carbon steel having a diameter of 75 mm and a height of 900 mm was charged with 100 parts of metallic silicon powder, 5 parts of a catalyst in the form of copper oxide powder, and 0.20 part of tetrakis[tris(dimethylamino)phosphoranylideneamino]-phosphonium chloride $[((CH_3)_2N)_3PN]_4PCl$. Then a gas mixture of methyl chloride and nitrogen was introduced into the reactor at a rate of 14.4 Nl/min and the reactor was heated at a temperature of 320° C. whereupon reaction continued. A mixture of metallic silicon powder and the catalyst was fed from the reactor bottom so as to keep constant the amount of the contact mass in the reactor. Reaction was continued for 6 hours, following which the reaction was terminated. The run was repeated 2 times. Reported in Table 1 are the concentrations of impurities in the metallic silicon used, an average of silane formation rate from the start to the end of reaction, and an average of cumulative content of useful silane.

Comparative Example 3

A fluidized bed reactor of carbon steel having a diameter of 75 mm and a height of 900 mm was charged with 100 parts of metallic silicon powder, 4 parts of a catalyst in the form of metallic copper powder, and 0.2 part of copper phosphide. Then a gas mixture of methyl chloride and nitrogen was introduced into the reactor at a rate of 14.4 Nl/min and the reactor was heated at a temperature of 310° C. whereupon reaction continued. Reaction was continued for 6 hours, following which the reaction was terminated. The run was repeated 3 times. Reported in Table 1 are the concentrations of impurities in the metallic silicon used, an average of silane formation rate from the start to the end of reaction, and an average of cumulative content of useful silane.

Comparative Example 4

A fluidized bed reactor of carbon steel having a diameter of 75 mm and a height of 900 mm was charged with 100 parts of metallic silicon powder and 4 parts of a catalyst in the form of metallic copper powder. Then a gas mixture of methyl chloride and nitrogen was introduced into the reactor at a rate of 14.4 Nl/min. Nitrogen gas was bubbled into a 0.1M toluene solution of trichlorophosphine to produce trichlorophosphine vapor, which was introduced into the reactor along with the nitrogen carrier. The reactor was heated at a temperature of 310° C. whereupon reaction continued. After 6 hours, the reaction was terminated. The run was repeated 3 times. Reported in Table 1 are the concentrations of impurities in the metallic silicon used, an average of silane formation rate from the start to the end of reaction, and an average of cumulative content of useful silane.

Comparative Example 5

A fluidized bed reactor of carbon steel having a diameter of 75 mm and a height of 900 mm was charged with 100 parts of metallic silicon powder and 4 parts of a catalyst in the form of metallic copper powder. Then a gas mixture of methyl chloride and nitrogen was introduced into the reactor at a rate of 14.4 Nl/min. Nitrogen gas was bubbled into a 0.1M toluene solution of trimethylphosphine to produce trimethylphosphine vapor, which was introduced into the reactor along with the nitrogen carrier. The reactor was heated at a temperature of 310° C. whereupon reaction continued. After 6 hours, the reaction was terminated. The run was repeated 3 times. Reported in Table 1 are the concentrations of impurities in the metallic silicon used, an average of silane formation rate from the start to the end of reaction, and an average of cumulative content of useful silane.

Comparative Example 6

A fluidized bed reactor of carbon steel having a diameter of 75 mm and a height of 900 mm was charged with 100 parts of metallic silicon powder and 4 parts of a catalyst in the form of metallic copper powder. Then a gas mixture of methyl chloride and nitrogen was introduced into the reactor at a rate of 14.4 Nl/min. Nitrogen gas was bubbled into a 0.1M toluene solution of monomethyldichlorosilane to produce monomethyldichlorosilane vapor, which was introduced into the reactor along with the nitrogen carrier. The reactor was heated at a temperature of 310° C. whereupon reaction continued. After 6 hours, the reaction was terminated. The run was repeated 3 times. Reported in Table 1 are the concentrations of impurities in the metallic silicon used, an average of silane formation rate from the start to the end of reaction, and an average of cumulative content of useful silane.

TABLE 1

| Example | Reaction temperature (°C.) | Fe (%) | Al (%) | Ca (%) | Additive | Additive concentration[1] (%/Si) | Formation rate[2] (g/h) | Useful silane content[3] (%) |
|---|---|---|---|---|---|---|---|---|
| Comparative Example 1 | 310 | 0.26 | 0.13 | 0.07 | none | — | 276 | 87.7 |
| Comparative Example 2 | 320 | 0.28 | 0.14 | 0.06 | none | — | 259 | 85.9 |
| Example 1 | 310 | 0.28 | 0.12 | 0.06 | tetraethylphosphonium chloride | 0.15 | 481 | 90.2 |
| Example 2 | 320 | 0.28 | 0.17 | 0.06 | tetraethylphosphonium chloride | 0.15 | 429 | 88.3 |
| Example 3 | 310 | 0.28 | 0.12 | 0.06 | tetraethylphosphonium chloride | 0.05 | 411 | 89.9 |
| Example 4 | 320 | 0.27 | 0.17 | 0.07 | tetraethylphosphonium chloride | 0.05 | 464 | 87.9 |
| Example 5 | 310 | 0.28 | 0.12 | 0.06 | tetrabutylphosphonium chloride | 0.24 | 674 | 90.9 |
| Example 6 | 320 | 0.27 | 0.17 | 0.07 | tetrabutylphosphonium chloride | 0.24 | 573 | 89.2 |
| Example 7 | 310 | 0.27 | 0.11 | 0.09 | tetrabutylphosphonium chloride | 0.06 | 606 | 90.3 |
| Example 8 | 320 | 0.27 | 0.14 | 0.07 | tetrabutylphosphonium chloride | 0.06 | 508 | 89.7 |
| Example 9 | 310 | 0.27 | 0.11 | 0.09 | tetraphenylphosphonium chloride | 0.30 | 531 | 89.6 |
| Example 10 | 320 | 0.27 | 0.14 | 0.07 | tetraphenylphosphonium chloride | 0.30 | 512 | 88.1 |
| Example 11 | 310 | 0.28 | 0.12 | 0.06 | tetraphenylphosphonium chloride | 0.05 | 574 | 88.8 |
| Example 12 | 320 | 0.25 | 0.18 | 0.06 | tetraphenylphosphonium chloride | 0.05 | 527 | 88.7 |
| Example 13 | 330 | 0.28 | 0.12 | 0.06 | tetramethylphosphonium chloride | 0.10 | 405 | 87.4 |
| Example 14 | 340 | 0.25 | 0.18 | 0.07 | tetramethylphosphonium chloride | 0.10 | 388 | 88.4 |
| Example 15 | 320 | 0.28 | 0.12 | 0.06 | tetrakis[tris(dimethylamino)phosphoranylideneamino] phosphonium chloride | 0.30 | 639 | 88.1 |
| Example 16 | 320 | 0.25 | 0.16 | 0.08 | tetrakis[tris(dimethylamino)phosphoranylideneamino] phosphonium chloride | 0.20 | 510 | 89.9 |
| Comparative Example 3 | 310 | 0.26 | 0.13 | 0.07 | copper phosphide | 0.20 | 276 | 89.8 |
| Comparative Example 4 | 310 | 0.26 | 0.13 | 0.07 | phosphorus trichloride | d) | 161 | 88.0 |
| Comparative Example 5 | 310 | 0.28 | 0.12 | 0.06 | trimethylphosphine | d) | 138 | 89.6 |
| Comparative Example 6 | 310 | 0.26 | 0.13 | 0.07 | monomethyldichlorosilane | d) | 288 | 87.7 |

Note:
[1])The concentration (wt %) of additive based on the weight of silicon.
[2]), [3])an average of 6 runs for Comparative Example 1, an average of 2 runs for Examples 1–16 and Comparative Example 2, and an average of 3 runs for Comparative Examples 3–6.
[4])In Comparative Examples 4–6, the additive was introduced into the reactor along with methyl chloride by bubbling nitrogen gas into a 0.1M toluene solution of the additive for carrying its vapor with nitrogen gas.

There has been described an industrial process for preparing organohalosilanes using a contact mass containing an effective amount of a phosphonium compound, thereby drastically increasing the formation rate and the utilization of silicon without lowering the selectivity of useful silane.

Japanese Patent Application No. 2001-261759 is incorporated herein by reference.

Reasonable modifications and variations are possible from the foregoing disclosure without departing from either the spirit or scope of the present invention as defined by the claims.

What is claimed is:

1. A process for preparing organohalosilanes of the following general formula (I):

$$R^1{}_nH_mSiX_{4-n-m} \qquad (I)$$

wherein $R^1$ is a monovalent hydrocarbon group, X is a halogen atom, n is an integer of 1 to 3, m is an integer of 0 to 2, and the sum of n and m is an integer of 1 to 3, by reacting metallic silicon particles with an organohalide in the presence of a copper catalyst, a contact mass composed of the metallic silicon and the catalyst further containing an effective amount of a phosphonium compound having on the molecule at least one group of the following general formula (II):

$$[R^2R^3R^4P\!-\!]^+Y^- \qquad (II)$$

wherein $R^2$, $R^3$ and $R^4$ are each independently a monovalent hydrocarbon group and Y is a halogen atom or acid group.

2. The process of claim 1 wherein the phosphonium compound has the following general formula (III):

$$[R^5R^6R^7R^8P]^+Y^- \qquad (III)$$

wherein $R^5$, $R^6$, $R^7$ and $R^8$ are each independently a monovalent hydrocarbon group and Y is as defined above.

3. The process of claim 1 wherein the phosphonium compound has the formula: $R^9{}_4PCl$ wherein $R^9$ is a $C_{1-4}$ alkyl or phenyl group or $[(R^{10}{}_2N)_3PN]_4PCl$ wherein $R^{10}$ is a $C_{1-4}$ alkyl group.

4. The process of claim 1 wherein the contact mass further contains at least one co-catalyst selected from the group consisting of metallic zinc, zinc compounds, metallic tin, tin compounds, metallic antimony, antimony compounds, metallic aluminum, aluminum compounds, metallic phosphorus, and phosphorus compounds (excluding phosphonium compounds).

* * * * *